United States Patent [19]

Logan

[11] Patent Number: 4,990,785

[45] Date of Patent: Feb. 5, 1991

[54] RADIATION IMAGING APPARATUS AND METHODS

[75] Inventor: K. William Logan, Boone County, Mo.

[73] Assignee: The Curators of the University of Missouri, Columbia, Mo.

[21] Appl. No.: 375,361

[22] Filed: Jul. 3, 1989

[51] Int. Cl.$^5$ .................... G01T 1/20; G01T 1/202
[52] U.S. Cl. .............. 250/368; 250/363.01; 250/363.02; 250/363.04; 250/367
[58] Field of Search ............. 250/363.01, 363.02, 250/363.04, 367, 368

[56] References Cited

U.S. PATENT DOCUMENTS

| | | | |
|---|---|---|---|
| 3,919,556 | 11/1975 | Berninger | 250/366 |
| 3,970,853 | 7/1976 | Kuhl et al. | 250/363 |
| 4,074,135 | 2/1978 | Stevens | 250/363.02 X |
| 4,228,515 | 10/1980 | Genna et al. | 364/571 |
| 4,755,680 | 7/1988 | Logan | 250/363.04 X |

FOREIGN PATENT DOCUMENTS

| | | | |
|---|---|---|---|
| 0175272 | 10/1982 | Japan | 250/363.02 |
| 1368821 | 10/1974 | United Kingdom | 250/363.02 |

OTHER PUBLICATIONS

Davis and Martone, "The Hybrid Radioisotope Scanner" vol. 7, 1966, pp. 114-127.
Dahlbom and Hoffman, "An Evaluation of a Two-Dimensional Array Detector for High Resolution PET", vol. 7, 1988, pp. 264-272.
Grenier, Bender and Jones, "A Computerized Multi-Crystal Scintillation Gamma Camera", vol. 2, 1974, pp. 101-111.
Gottschalk et al., "Diagnostic Nuclear Medicine", 1976, pp. 97, 98 and 103.
Sorenson, et al., "Physics in Nuclear Medicine", Second Edition, 1987, pp. 318-321.
Siemens, "The Technical Edge Nuclear Medicine Gamma Camera Systems", Nov., 1985, pp. 1-28.

Primary Examiner—Constantine Hannaher
Assistant Examiner—Jacob M. Eisenberg
Attorney, Agent, or Firm—Senniger, Powers, Leavitt & Roedel

[57] ABSTRACT

Radiation imaging apparatus includes first and second bodies of material capable of producing scintillations in response to bombardment by ionizing radiation, each scintillation producing body having a surface bordered in part by an edge, the edge of the first body adjacent the edge of the second body. The radiation imaging apparatus also includes joining members located between the edges of the first and second bodies for transmitting light emitted from the edges of the first and second bodies as a result of scintillations produced by the first and second bodies, a collimator for collimating the ionizing radiation, and photomultiplier tubes for converting the scintillations to electrical outputs including a plurality of scintillation sensing units on the first and second scintillation producing bodies and on the joining body.

33 Claims, 5 Drawing Sheets

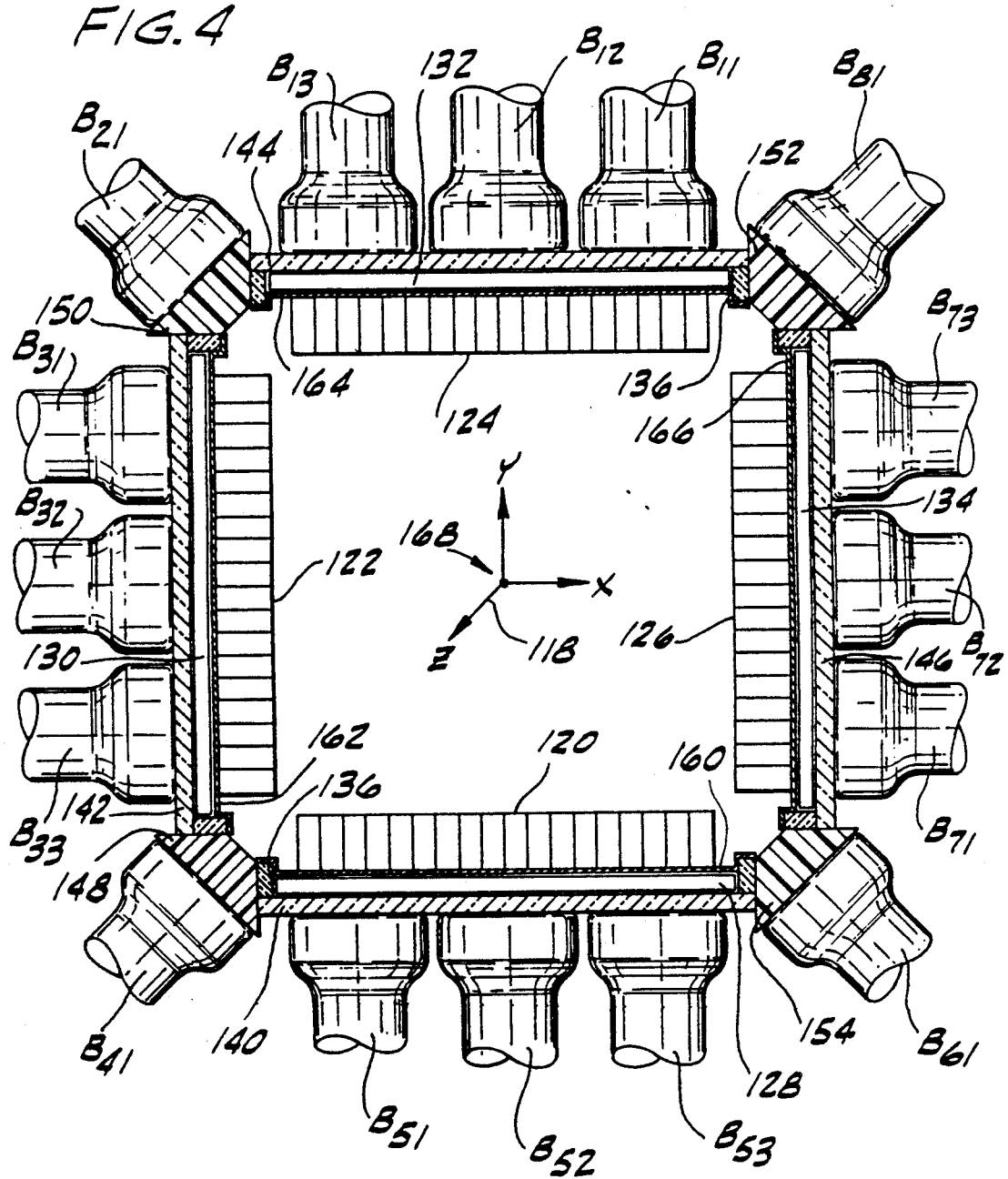

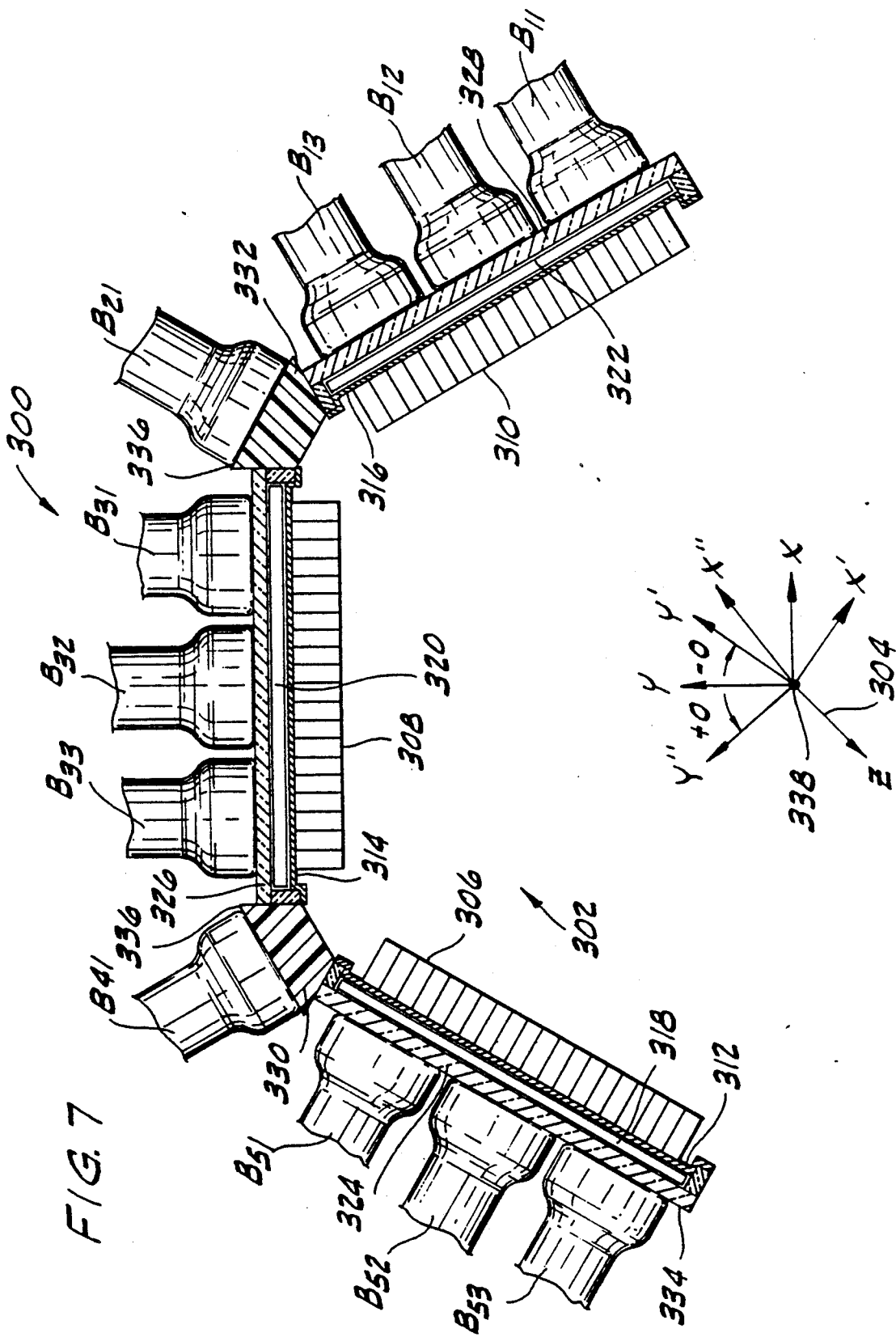

RADIATION IMAGING APPARATUS AND METHODS

BACKGROUND OF THE INVENTION

The present invention relates to radiation imaging apparatus and more particularly to radiation imaging apparatus involving a scintillation body having a rectangular cross-section with scintillation sensing units disposed along the body.

Positron emission tomography (PET) brain imaging systems are used in nuclear medicine diagnostic procedures for providing images of the brain. The cost of a PET system is very high and its use in clinical studies is limited to a few institutions which can afford one. An alternative to the PET systems is the single photon emission computed tomography (SPECT) imaging system. The SPECT system includes a scintillation camera for detecting gamma rays emitted from a patient who has been administered a radiopharmaceutical. The SPECT system converts the detected gamma rays to tomographic images of the particular organ or region of the patient's body being analyzed. Although the SPECT system produces tomographic images which contain interpretable perfusion data, the low sensitivity, prolonged data acquisition times, poor resolution, and inability to perform absolute quantitation from the data makes the resulting studies less valuable than comparable PET studies. In order to overcome these deficiencies several systems have been designed and produced to improve SPECT brain imaging. Some of these systems are the Medimatic Tomomatic 564 manufactured by Medimatic Division of M.I.D., Inc., Irvine, Calif. and the Multi-X 810 manufactured by Strichman Medical Equipment Inc., Medfield, Mass. However, these systems can cost two to four times the cost of a SPECT imaging system which limits the number of institutions which can purchase one.

Another system which has been designed and produced to improve SPECT brain imaging is disclosed in U.S. Pat. No. 4,755,680 incorporated by reference. In this patent a radiation imaging apparatus includes a scintillation crystal which is a substantially tubular body of material such as crystalline sodium iodide. Manufacturing a tubular scintillator adds to the cost of the system as compared to using flat scintillators which are readily available.

SUMMARY OF THE INVENTION

Among the objects of the present invention is the provision of a radiation imaging apparatus which has a simple structure and is relatively economical to manufacture and use; the provision of such a radiation imaging apparatus which utilize or require relatively few photomultiplier tubes or other photosensitive devices and associated electronics; the provision of such a radiation imaging apparatus which allows portions of the detector assembly collecting data to be positioned close together when imaging a common source volume; and the provision of such a radiation imaging apparatus which uses an angle assembly to join two flat scintillation crystals into a non-planar detector assembly to facilitate viewing a common source volume.

Generally, a radiation imaging apparatus includes first and second means for producing scintillations in response to bombardment by ionizing radiation, each scintillation producing means having a surface bordered in part by an edge, and the edge of the first means adjacent the edge of the second means. The radiation imaging apparatus also includes joining means located between the edges of the first and second means for transmitting light emitted from the edges of the first and second means as a result of scintillations produced by the first and second means, means for collimating the ionizing radiation, and means for converting the scintillations to electrical outputs including a plurality of scintillation sensing units on the first and second scintillation producing means and on the joining means.

In general, another form of the invention involves radiation imaging apparatus for use with a specimen emitting ionizing radiation including a scintillation assembly having a common axis along which the specimen is positioned and including a plurality of bodies having a substantially rectangular surface parallel to the common axis for producing scintillations in response to bombardment by the ionizing radiation from the specimen, each surface bordered in part by an edge and joining means located between adjacent edges of the bodies for joining the bodies in an open ended box-like structure substantially coaxial with the common axis, the joining means for transmitting light emitted from the edges of the bodies as a result of scintillations produced by the bodies. The imaging apparatus also includes means for collimating the ionizing radiation and means for converting the scintillations to electrical outputs including a plurality of scintillation sensing units located on the outside of the bodies and the joining means.

Other objects and features will be in part apparent and in part pointed out hereinafter.

BRIEF DESCRIPTION OF THE DRAWINGS

FIG. 4 is a cross-sectional view taken along the plane of line 4—4 of FIG. 3A;

FIG. 7 is a partially pictorial and partially block diagrammatic representation of another embodiment of a radiation imaging apparatus of the present invention.

Corresponding reference characters indicate corresponding parts throughout the several views of the drawings.

DETAILED DESCRIPTION OF THE PREFERRED EMBODIMENT

Figure 1:
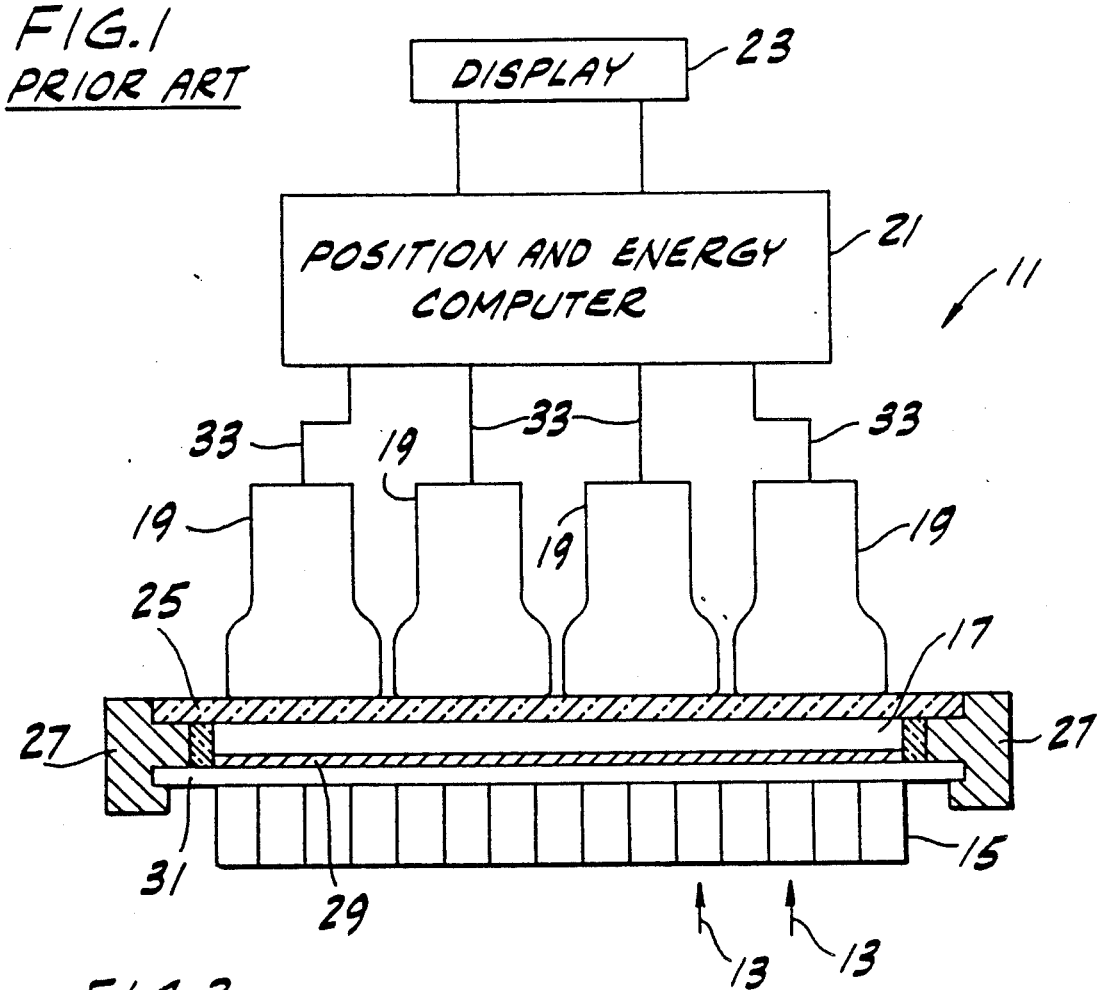
FIG. 1 is a partially pictorial and partially block diagrammatic representation of a prior art radiation imaging apparatus.

Referring now in particular to FIG. 1, there is shown the essential components of a prior art photomultiplier type gamma camera 11. Gamma rays, indicated by arrows 13, emitted by a patient (not shown) undergoing a nuclear medical examination, are collimated in a suitable collimator 15 which may typically be a parallel hole collimator fabricated of lead. The collimated gamma rays are then absorbed by a scintillator 17 which is typically formed of a single crystal of sodium iodide in the form of a disk of thin dimension. The pulse of light resulting from each scintillation event in scintillator 17 is viewed by an array of photomultiplier tubes (PMTs) 19. The output signals of the PMTs 19 are resolved in electronic circuitry 21, such as a computer, to provide electrical signals proportional to the position of the scintillation event and the energy of the absorbed gamma ray. The processed electrical signals are displayed on a suitable image display device 23, such as a conventional storage oscilloscope. Collimator 15 is suitably fastened to the outside of the open input end of a light-tight housing (not shown). Scintillator 17 is disposed at the open end of housing and is supported along its output face by being sealed to a glass plate 25, such as a UV transmitting glass for example Pyrex (trademark), that has its peripheral surface sealed to a flange 27 at the open end of the housing. Scintillator 17 is also sealed along its peripheral surface to flange 27. Light loss from the scintillator input face is minimized by packing the input face crystal surface with a suitable material 29, such as magnesium oxide powder, in order to make the crystal surface highly light-reflective. The side surface of scintillator 17 may also be made highly reflective or highly light-absorbing, as desired. An aluminum window 31 is interposed between collimator 15 and the reflective coating 29 on the input face of scintillator 17. The aluminum window 31, glass plate 25, and scintillator 17 are sealed within flange 27 and scintillator 17 is sealed to the glass plate 25. The housing is backed with lead to provide shielding against extraneous gamma rays. The array of PMTs 19 is supported by a metal plate member (not shown) fastened to a flange (not shown) along the inner surface of the housing near the closed output end. The output end of the housing may also be enclosed by lead shielding and other material which will prevent gamma rays and ambient light from entering the housing through the output end. Electrically insulated conductors 33 pass through the output end of the housing and are connected to the computer 21. Signals from the PMTs 19 are supplied to the computer 21 for processing. The processed signals are then supplied to the display 23.

Figure 2:
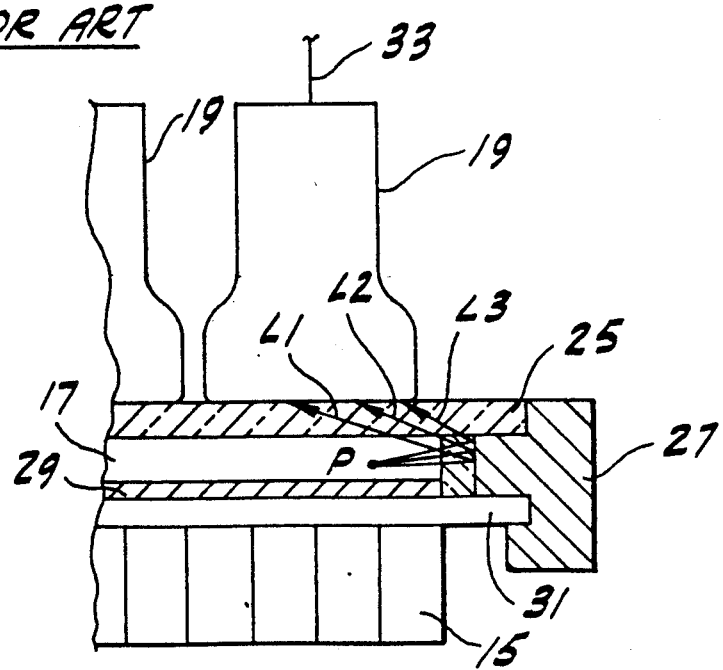
FIG. 2 is an enlarged partially broken away view of the right hand side of the radiation imaging apparatus of FIG. 1 with a scintillation event at the right side.

FIG. 2 shows a photon event P occurring near the edge of the scintillator crystal 17. The light rays $L_1$, $L_2$, and $L_3$ produced by photon event P in the scintillator 17 are reflected at the edge of the scintillator 17 and are transmitted through the glass plate 25 to the PMTs 19. The PMTs 19 produce a number of electronic signals of varying amplitudes in response to the intensity of the light sensed. The light rays $L_1$, $L_2$, and $L_3$ are nonlinear due to reflecting off the edge of the scintillator 17. The nonlinearity of the light rays $L_1$, $L_2$, and $L_3$ results in a signal which cannot be accurately positioned by the computer. This nonlinearity is termed edge packing. Edge packing results from a somewhat greater light collection efficiency for events near the edge versus central regions of the detector crystals as a result of internal reflections of scintillation light from the sides of the detector crystal back into the PMTs near the edge. Also, events occurring toward the center of the crystal have PMTs on either side of the event location whereas at the edges of the crystals there are PMTs only to one side.

The part of the image having nonlinearity usually is masked on the display and therefore is not a part of the useful imaging area. Typically, 5 cm or more of the detector assembly is eliminated by the mask. This reduces the efficient use of the PMTs and the crystal area.

Figure 3A:
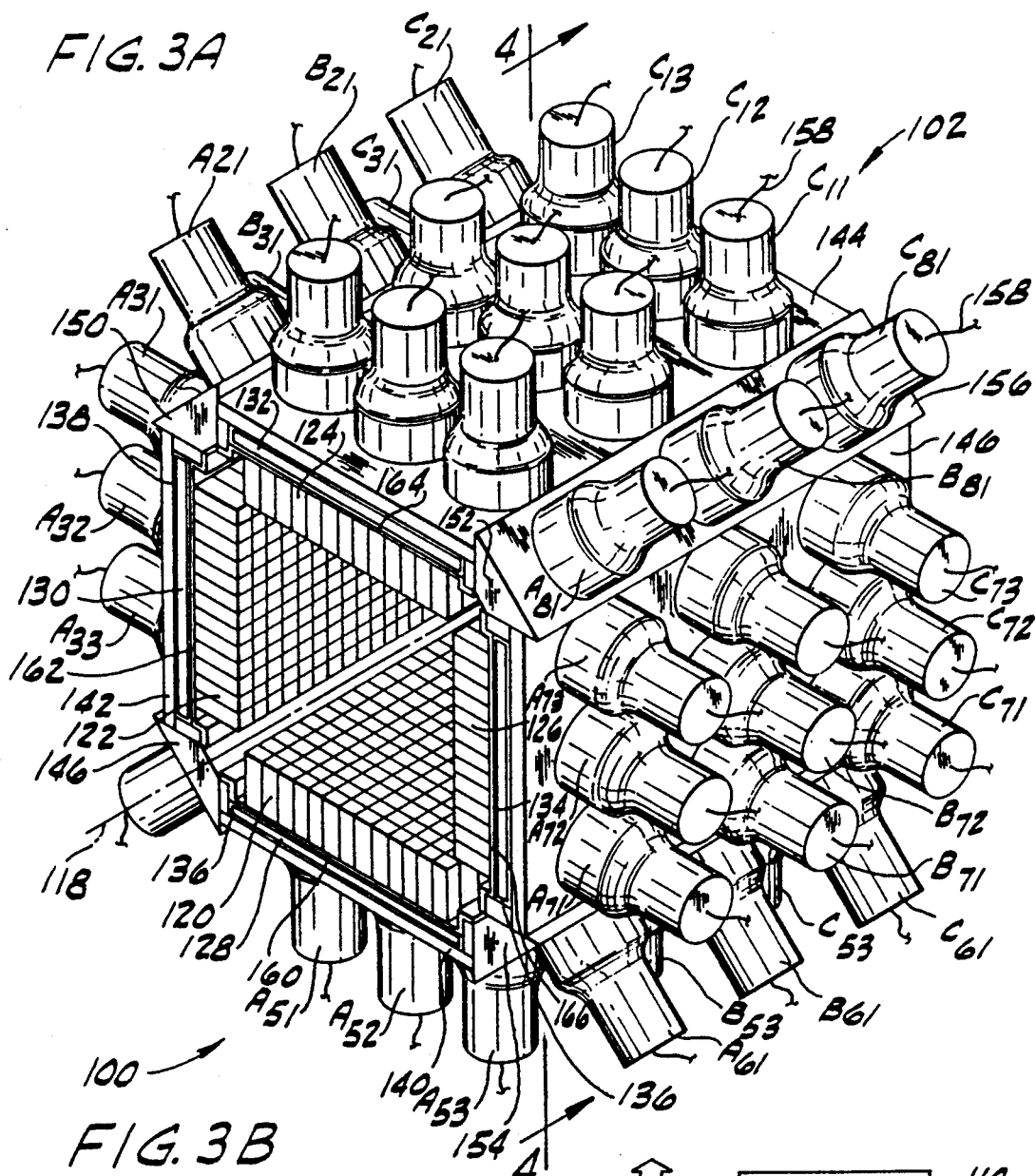
FIGS. 3A and 3B are a partially pictorial and partially block diagrammatic representation of a radiation imaging apparatus of the present invention.
Figure 3B:
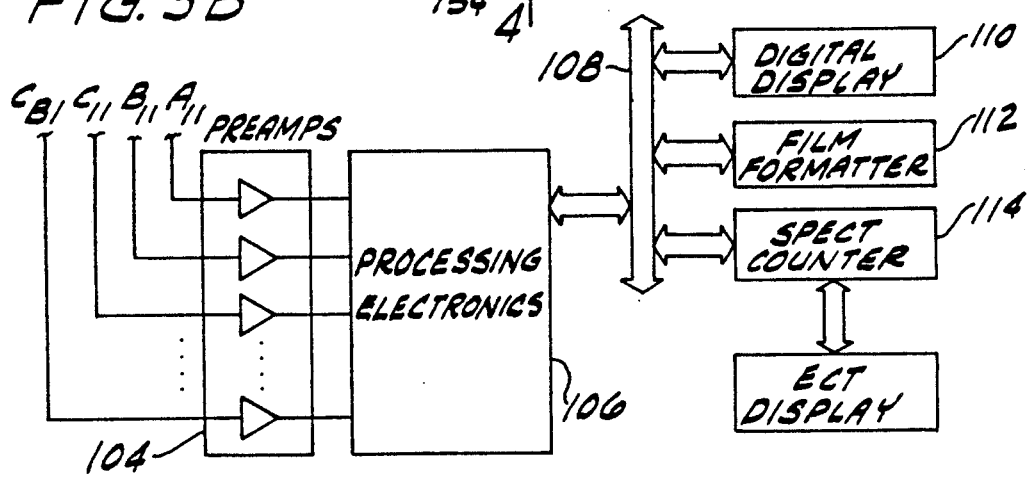

In FIG. 3A, one preferred embodiment of a radiation imaging apparatus of the present invention is shown as a photon imaging apparatus 100. Apparatus includes a detector assembly 102 connected to preamplifier array 104, and processing electronics 106 as shown in FIG. 3B. The processing electronics 106 are coupled to a bus 108 and communicate with a digital real time display 110 and film formatter 112 for showing non-tomographic images. The processing electronics 106 also communicate on bus 108 with a Single Photon Emission Computed Tomography (SPECT) computer 114, to which is attached an Emission computed Tomography (ECT) display unit 116. The SPECT computer 114 and ECT display unit 116 are commercially available equipment, such as the ADAC Laboratories System 3300 SPECT computer system from ADAC Laboratories, Sunnyvale, Calif. Digital real time display apparatus 110 may be any commercially available products such as a PDP 11/23 computer from Digital Equipment Corporation, Boston, Mass., outfitted with digital display output circuits Model IP 512 and Model AP 512 from Imaging Technology, Inc., Woburn, Mass., to a video monitor such as Model SNA 15 from Conrac Corporation, Covina, Calif. Film formatter 112 is also a commercially available product such as Matrix Video Imager, Model $M^2$, from Matrix Instruments, Inc., Northvale, N.J.

Referring to FIGS. 3A and 4, the detector assembly 102 has a common axis 118 along which a specimen (not shown) for emitting ionizing radiation is located. The detector assembly 102 includes collimators 120, 122, 124, and 126 adjacent to scintillators 128, 130, 132, and 134. The collimators 120-126 constitute means for collimating ionizing radiation. Each of the scintillators 128-134 is a planar body substantially parallel to the common axis 118. The periphery of each of the scintillators 128-134 terminates in a surface bordered in part by an edge 136. The scintillators 128-134 comprise crystals each having a substantially rectangular cross-section in a plane substantially parallel to the common axis 118 and each having substantially planar exterior faces 138. The scintillation crystals 128-134 are formed of a material such as crystalline sodium iodide (NaI) or bismuth germanate ($Bi_4Ge_3O_{12}$). The patient or a body part of the patient which constitutes a specimen is placed along axis 118 within the detector assembly 102. A patient is administered a radiopharmaceutical drug labeled with radioactive isotope such as Technetium-99 m which emits gamma rays at an energy level of 140 kilo-electron volts (KeV). The ionizing radiation bombards and inelastically collides with the crystalline material of the scintillators 128-134 to produce a scintillation or photon event.

Optical windows 140, 142, 144, and 146 are adjacent each of the planar exterior faces 138 of each of the scintillators 128-134, respectively. The windows 140-146 have substantially planar exterior surfaces. The windows 140-146 are an example of light transmissive means. Corner bridges 148, 150, 152, and 154, each in the shape of a prism are positioned between a pair of adjacent edges 136 of the scintillators 128-134. The bridges 148-154 each have a substantially triangular cross-section in a plane substantially perpendicular to the axis 118 and have a substantially planar exterior face 156 parallel to the axis 118. The bridges 148-154 are formed of glass, UV transmitting glass (e.g., Pyrex (trademark)), plexiglas, or plastic, or sodium iodide (NaI). The bridges 148-154 are an example of joining means located between the edges of the scintillators for transmitting light emitted from the edges of the crystals as a result of scintillations produced by the crystals.

By virtue of the construction of the detector assembly 102, the photons emanating from a scintillation event reach in varying proportions to at least some of photomultiplier tubes (PMTs) $A_{11}$, $A_{12}$, $A_{13}$, $B_{11}$, $B_{12}$, $B_{13}$, $C_{11}$, $C_{12}$, $C_{13}$, $A_{21}$, $B_{21}$, $C_{21}$, $A_{31}$, $A_{32}$, $A_{33}$, $B_{31}$, $B_{32}$, $B_{33}$, $C_{31}$, $C_{32}$, $C_{33}$, $A_{41}$, $B_{41}$, $C_{41}$, $A_{51}$, $A_{52}$, $A_{53}$, $B_{51}$, $B_{52}$, $B_{53}$, $C_{51}$, $C_{52}$, $C_{53}$, $A_{61}$, $B_{61}$, $C_{61}$, $A_{71}$, $A_{72}$, $A_{73}$, $B_{71}$, $B_{72}$, $B_{73}$, $C_{71}$, $C_{72}$, $C_{73}$, $A_{81}$, $B_{81}$, and $C_{81}$. Some of the PMTs are not shown in FIG. 3A for purposes of clarity. The PMTs constitute means for converting the scintillations to electrical outputs. The PMTs are positioned on the exterior surfaces of the windows 140–146 and on the exterior surfaces 156 of the bridges 148–154. The PMTs are connected to the preamplifiers 104 via lines 158. As shown, the PMTs are arranged in a 3×3 matrix on each of the windows 140–146. There are also 3 PMTs arranged on the exterior surface 156 of each of the bridges 148–154.

FIG. 4 shows a vertical cross-section through the detector assembly 102 along line 4—4 of FIG. 3A, i.e., perpendicular to axis 118. The detector assembly 102 includes the collimators 120–126, the scintillators 128–134, optical windows 140–146, and corner bridges 148–154. The detector assembly 102 also includes aluminum windows 160, 162, 164, and 166 positioned between each of the collimators 120–126 and the scintillators 128–134, respectively.

The position and energy of each photon event is analyzed with reference to a three dimensional rectangular coordinate system with the origin point located at the center of the detector assembly 102. An X-Y-Z rectangular coordinate system 168 is orientated having its Z axis coincident with axis 118. The various PMTs locations range symmetrically from negative to positive values for all three coordinates (X, Y, Z). The two scintillators 130 and 134 are located on and perpendicular to the X axis, and the two scintillators 128 and 132 are located on and perpendicular to the Y axis.

Figure 5:
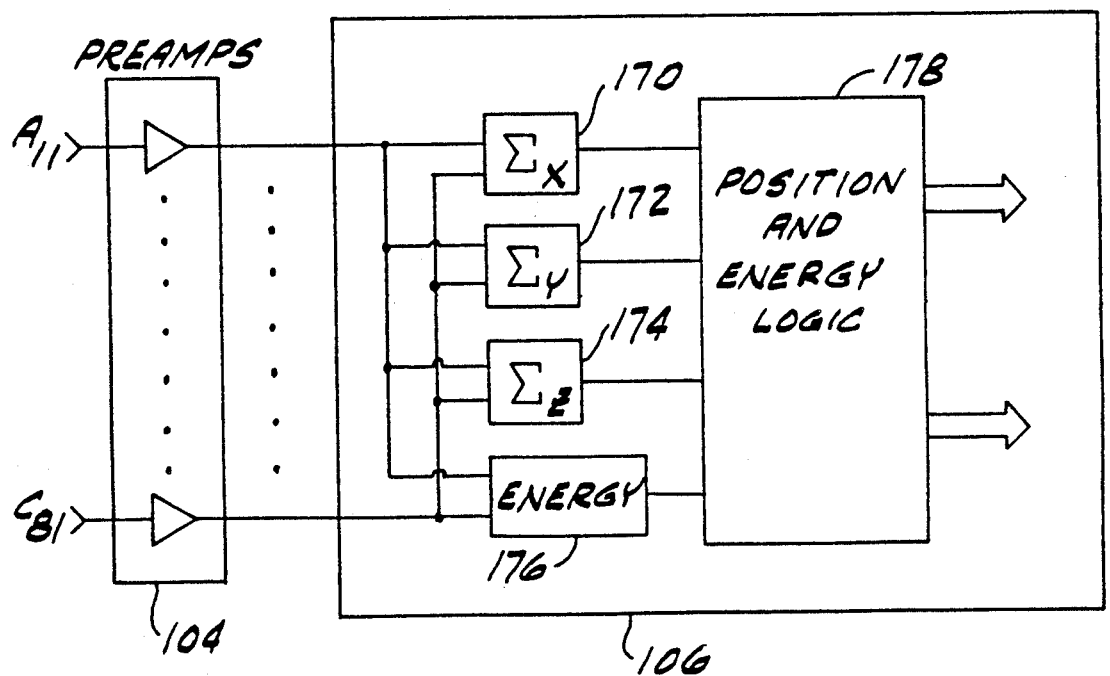
FIG. 5 is a block diagram of the processing electronics of the radiation imaging apparatus of FIG. 3B.

With reference to FIG. 5, the electrical signal produced by each of the PMTs for a given photon event is buffered by its associated preamplifier in the preamplifier array 104 and provided to three different position summing circuits 170, 172, and 174 and an energy circuit 176 in the processing electronics 106. A position dependent weighting factor is applied to each of the signals in the three position summing circuits 170–174. The values of the weighting factors are approximately proportional to the values of the position coordinates of the PMT generating the signal. There is an X position weighting factor for each of the PMTs that is applied to the signals in the X summing circuit 170. In similar manner, there are Y and Z weighting factors for each PMT used in the Y position summing circuit 172 and the Z position summing circuit 174.

For example, the two scintillators 128 and 132 located on and perpendicular to the Y axis have a range of relative X position coordinate weighting factors for the PMTs located on optical windows 140 and 144 of −1, 0, and +1. The Y position coordinate weighting factors for these two scintillators 128 and 132 are −2 and +2 since these two scintillators 128 and 132 are perpendicular to the Y axes and displaced essentially two units from the origin point due to the size of the scintillators in the detector assembly 102. Additionally, the range of the relative Z position coordinate weighting factors is −1, 0, +1. The sets of weighting factor values for the nine PMTs on the windows 140 and 144 are: (−1, −2, −1) for PMT $A_{51}$; (−1, −2, 0) for PMT $B_{51}$; (−1, −2, 1) for PMT $C_{51}$; (0, −2, −1) for PMT $A_{52}$; (0, −2, 0) for PMT $B_{52}$; (0, −2, 1) for PMT $C_{52}$; (1, −2, −1) for PMT $A_{53}$; (1, −2, 0) for PMT $B_{53}$; (1, −2, 1) for PMT $C_{53}$; (1, 2, −1) for PMT $A_{11}$; (1, 2, 0) for PMT $B_{11}$; (1, 2, 1) for PMT $C_{11}$; (0, 2, −1) for PMT $A_{12}$; (0, 2, 0) for PMT $B_{12}$; (0, 2, 1) for PMT $C_{12}$; (−1, 2, −1) for PMT $A_{13}$; (−1, 2, 0) for PMT $B_{13}$; and (−1, 2, 1) for PMT $C_{13}$.

In a similar manner the weighting factors are assigned for the PMTs on the other windows 142 and 146. On window 146 the X position coordinate weighting factors will be +2 for all the PMTs. On other window 142 the X position coordinate weighting factors will be −2 for all the PMTs. The range of the Y and Z position coordinates weighting factors for both windows 142 and 146 is −1, 0, +1. In particular, the sets of weighting factor values for the nine PMTs on the windows 142 and 146 are: (−2, 1, −1) for PMT $A_{31}$; (−2, 1, 0) for PMT $B_{31}$; (−2, 1, 1) for PMT $C_{31}$; (−2, 0, −1) for PMT $A_{32}$; (−2, 0, 0) for PMT $B_{32}$; (−2, 0, 1) for PMT $C_{32}$; (−2, −1, −1) for PMT $A_{33}$; (−2, −1, 0) for PMT $B_{33}$; (−2, −1, 1) for PMT $C_{33}$; (2, −1, −1) for PMT $A_{71}$; (2, −1, 0) for PMT $B_{71}$; (2, −1, 1) for PMT $C_{71}$; (2, 0, −1) for PMT $A_{72}$; (2, 0, 0) for PMT $B_{72}$; (2, 0, 1) for PMT $C_{72}$; (2, 1, −1) for PMT $A_{73}$; (2, 1 0) for PMT $B_{73}$; and (2, 1, 1) for PMT $C_{73}$.

For the PMTs mounted on the corner bridges 148–154, the Z position coordinate weighting factors range is −1, 0, and +1. The PMTs on any one of the corner bridges 148–154 will have the same X and Y values for the weighting factors since each corner bridge is parallel to the Z axis. The weighting factors for the PMTs on corner bridges 148–154 are as follows: (−2, 2, −1) for PMT $A_{21}$; (−2, 2, 0) for PMT $B_{21}$; (−2, 2, 1) for PMT $C_{21}$; (−2, −2, −1) for PMT $A_{41}$; (−2, −2, 0) for PMT $B_{41}$; (−2, −2, 1) for PMT $C_{41}$; (2, −2, −1) for PMT $A_{61}$; (2, −2, 0) for PMT $B_{61}$; (2, −2, 1) for PMT $C_{61}$; (2, 2, −1) for PMT $A_{81}$; (2, 2, 0) for PMT $B_{81}$; (2, 2, 1) for PMT $C_{81}$.

The processing electronics 106 also include a position and energy logic circuit 178 which determines in which of the scintillators a given photon event occurred. A scintillator having a photon event is identified by analyzing the net X and net Y signals, as normalized to the total light measured by all of the PMTs for each photon event by the energy circuit 176. The total light measurement for each photon event is determined by taking the simple unweighted sum of all the outputs of the PMTs. This represents the relative energy signal for the event. If the photon event is in one of the scintillators 130 or 134 located on and perpendicular to the X axis, then the normalized net X signal will be either 2 due to the X position coordinate weighting factor being the same for all the PMT's on scintillator 134 or −2 due to the X position coordinate weighting factor being the same for all the PMT's on scintillator 130. If the photon event is not in one of these scintillators 130 or 134, then the normalized net X signal will be either in the range of −1 to +1 depending on the position with respect to the X-axis. Alternately, if the photon event is in one of the scintillators 128 or 132 located on and perpendicular to the Y axis, then the normalized net Y signal will be either 2 or −2.

Once it is determined from either the normalized net X or Y signal in which scintillator the photon event occurred, the position on the surface of the scintillator is determined by analyzing the other two position coordinates. For example, if the event is in one of the scintillators 130 or 134 located on and perpendicular to the X axis, then the position of the event on the surface of scintillator 134 is determined by analyzing the normalized net Y and Z signals. If the event occurs in one of the two scintillators 128 or 132 located on and perpendicular to the Y axis, then the position of the event on the surface of the scintillator is determined by analyzing the normalized net X and Z signals.

Once the position and energy signals have been determined by the position and energy logic, the signals are provided over bus 108 to the display 110.

Figure 6:
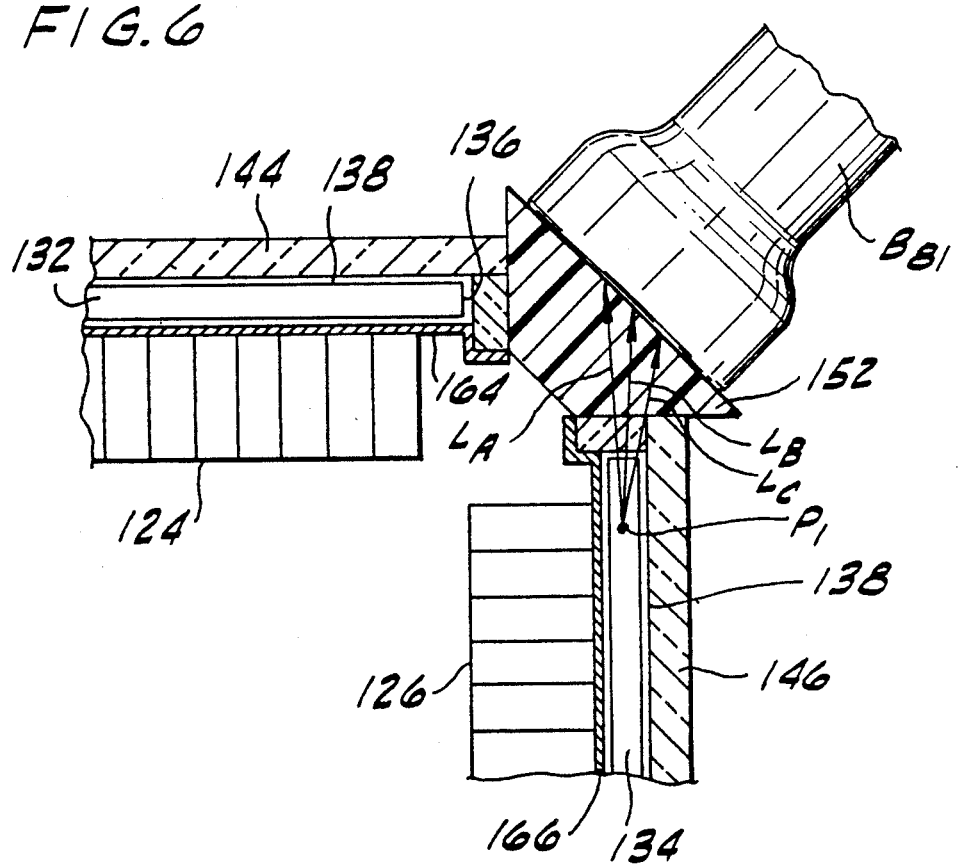
FIG. 6 is a scintillation event at an edge of the radiation imaging apparatus of FIG. 3A.

A photon event $P_1$ is shown in FIG. 6 occurring in scintillator crystal 134. The photon event causes the scintillator 134 to produce light such as light rays $L_A$, $L_B$, and $L_C$ from the absorbed photon event $P_1$. Some of the light energy passes through the edge 138 of the scintillator 134 and is collected by the corner bridge 152. The corner bridge 152 transmits the light energy to PMT $B_{81}$, which converts the light rays $L_A$, $L_B$, and $L_C$ into electrical signals. The corner bridge 152 transmits light at the edge of the scintillator crystal for detection by a PMT in contrast to conventional radiation imaging devices (FIG. 2) which reflect or absorb light at the edge. The use of the corner bridges enhance the total light measurement and allows accurate localization of photon events close to the edge of the scintillator crystals.

FIG. 7 shows another preferred embodiment of a radiation imaging apparatus of the present invention. Apparatus 300 includes a detector assembly 302, an array of amplifiers, processing electronics, and a display (all of which are not shown) similar to amplifiers 104, processing electronics 106, and display 110. The detector assembly 302 has a common axis 304 along which a specimen (not shown) for emitting ionizing radiation is located. The assembly 302 includes collimators 306, 308, 310 which are perpendicular to the axis 304, aluminum windows 312, 314, and 316, scintillators 318, 320, and 322, optical windows 324, 326, and 328, and corner bridges 330 and 332. An array of PMTs $B_{11}$, $B_{12}$, $B_{13}$, $B_{21}$, $B_{31}$, $B_{32}$, $B_{33}$, $B_{41}$, $B_{51}$, $B_{52}$, and $B_{53}$ is positioned adjacent an exterior surface 334 of each of the windows 324, 326, and 328 and an exterior surface 336 of each of the corner bridges 330 and 332. The array also includes PMTs $A_{11}$, $A_{12}$, $A_{13}$, $C_{11}$, $C_{12}$, $C_{13}$, $A_{21}$, $C_{21}$, $A_{31}$, $A_{32}$, $A_{33}$, $C_{31}$, $C_{32}$, $C_{33}$, $A_{41}$, $C_{41}$, $A_{51}$, $A_{52}$, $A_{53}$, $C_{51}$, $C_{52}$, and $C_{53}$ all of which are not shown in this cross-sectional view. The corner bridges 330 and 332 have a substantially trapezoidal cross-section substantially perpendicular to the common axis 304. The scintillators 318, 320, and 322 form an oblique angle having a vertex along an axis parallel to the common axis 304. Apparatus 300 is an example of a three view body imager used for tomographic imaging of the heart.

The PMT outputs for detector assembly 302 are measured and analyzed in a manner similar to that described for detector assembly 102. The position dependent weighting coefficients for PMT's on optical windows 324, 326, and 328, and corner bridges 330 and 332 are derived as follows.

It is possible to have a separate orthogonal coordinate system for each of the three windows 324, 326, and 328 as shown in FIG. 7. The three coordinate systems (X,Y,Z; X',Y',Z; and X",Y",Z) all have the same Z axis, and are otherwise related to each other by a rotation angle $\theta$. The common Z axis is coincident with axis 304. The coordinate system X',Y',Z differs from the coordinate system X,Y,Z only by rotation angle $-\theta$ around the Z axis and the coordinate system X",Y",Z differs from X,Y,Z only by rotation angle $+\theta$ around the Z axis.

The PMT locations on window 324 can be described by coordinates in coordinate system X',Y',Z, and window 324 can be described as centered on and perpendicular to the negative X' axis. PMT locations on window 326 can be described by coordinates in coordinate system X,Y,Z, and window 326 can be described as centered on and perpendicular to the positive Y axis. PMT locations on window 328 can be described by coordinate system X",Y",Z, and window 328 can be described as centered on and perpendicular to the positive X" axis.

The PMT's on window 324 all have a X' coordinate value of $-2$ since the window is perpendicular to X' and located two units from the origin 338. The Y' coordinates for PMT's on window 324 range from $-1, 0, 1$, and the Z coordinates range $-1, 0, 1$. In the X',Y',Z coordinate system, the PMT's on bridge 330 all have X' coordinate $-2$, and Y' coordinate $+2$; the Z coordinate for bridge 330 PMT's ranges $-1, 0, 1$.

For window 326, in the X, Y, Z coordinate system, all PMT's have a Y coordinate value of $+2$. X coordinate values range from $-1, 0, 1$, and Z coordinate values range from $-1, 0, 1$. In the X, Y, Z coordinate system the PMT's on bridge 330 have X coordinate values of $-2$, and Y coordinate values of $+2$, and Z coordinate values range from $-1, 0, +1$. Note that the numerical values from PMT coordinate positions on bridge 330 are the same in both the X', Y', Z and the X, Y, Z coordinate systems. The PMT's on bridge 336 have X values of $+2$, Y values of $+2$, and Z coordinate values range from $-1, 0, +1$.

In the X", Y", Z coordinate system, PMT's on window 328 all have X" values of $+2$, while Y' coordinate values range from $-1, 0, +1$ and Z coordinate values range from $-1, 0, +1$. the PMT's on bridge 336 all have X" coordinate values of $+2$, and Y" coordinate values of $+2$, while the Z coordinate ranges $-1, 0, +1$. Note that for the PMT's on bridge 336, the numerical values of the coordinates are the same in both the X,Y,Z and X",Y",Z coordinate systems.

As was done for detector assembly 102, the PMT position coordinates can be selected for the weighting factors for PMT's on detector assembly 302. The numerical value of the coordinates for PMT's on bridges 330 and 336 do not depend on the rotation angle $\theta$ and are the same in all three coordinate systems. In addition, there is essentially no transmission of light between crystals 318 and 320, or between crystals 322 and 318, or between crystals 318 and 322. Therefore from a functional point of view it is not necessary to electronically distinguish between X, X' and X", or between Y, Y', and Y". There can be one x summing circuit, one y summing circuit, and one z summing circuit.

The set of weighing factor values for the PMTs on the windows 324, 326, and 328 are: $(-2, -1, -1)$ for PMT $A_{53}$; $(-2, -1, 0)$ for PMT $B_{53}$; $(-2, -1, 1)$ for PMT $C_{53}$; $(-2, 0, -1)$ for PMT $A_{52}$; $(-2, 0, 0)$ for PMT $B_{52}$; $(-2, 0, 1)$ for PMT $C_{52}$; $(-2, 1, -1)$ for PMT $A_{51}$; $(-2, 1, 0)$ for PMT $B_{51}$; $(-2, 1, 1)$ for PMT $C_{51}$; $(-1, 2, -1)$ for PMT $A_{33}$; $(-1, 2, 0)$ for PMT $B_{33}$; $(-1, 2, 1)$ for PMT $C_{33}$; $(0, 2, -1)$ for PMT $A_{32}$; $(0, 2, 0)$ for PMT $B_{32}$; $(0, 2, 1)$ for PMT $C_{32}$; $(1, 2, -1)$ for PMT $A_{31}$; (1, 2, 0) for PMT $B_{31}$; (1, 2, 1) for PMT $C_{31}$; (2, 1, −1) for PMT $A_{13}$; (2, 1, 0) for PMT $B_{13}$; (2, 1, 1) for PMT $C_{13}$; (2, 0, −1) for PMT $A_{12}$; (2, 0, 0) for PMT $B_{12}$; (2, 0, 1) for PMT $C_{12}$; (2, −1, −1) for PMT $A_{11}$; (2, −1, 0) for PMT $B_{11}$; and (2, −1, 1) for PMT $C_{11}$.

The set of weighting factor values for the PMTs on the corner bridges 330 and 332 are as follows: (−2, 2, −1) for PMT $A_{41}$; (−2, 2, 0) for PMT $B_{41}$; (−2, 2, 1) for PMT $C_{41}$; (2, 2, −1) for PMT $A_{21}$; (2, 2, 0) for PMT $B_{21}$; and (2, 2, 1) for PMT $C_{21}$.

The processing electronics for detector assembly 302 may be similar to those described for detector assembly 102 above. The normalized net X, net Y and net Z signals can be analyzed for the position of a scintillation event. For example, if the net X value is −2, the event is located in crystal 318, and net Y and net Z signals give the location on the face of the crystal 318. If net X is +2, the event is located in crystal 322 and net Y and net Z signals are analyzed to determine the location of the event. If net Y is +2, then the event occurred in crystal 320, and analysis of the net X and net Z signals determine the event location on the face of the crystal.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Radiation imaging apparatus comprising:
   first and second means for producing scintillations in response to bombardment by ionizing radiation, each said scintillation producing means having a surface bordered in part by an edge, the edge of the first means adjacent the edge of the second means;
   joining means located between the edges of the first and second means for transmitting light emitted from the edges of the first and second means as a result of scintillations produced by the first and second means;
   means for converting light transmitted from the surface of the scintillation means and light transmitted by the joining means to electrical outputs including a plurality of scintillation sensing units on the first and second scintillation producing means and on the joining means.

2. The radiation imaging apparatus of claim 1 further comprising means for collimating the ionizing radiation bombarding the first and second means substantially perpendicular to a common axis.

3. The radiation imaging apparatus of claim 2 wherein the first and second means comprise planar bodies substantially parallel to the common axis along which a specimen for emitting ionizing radiation is located and each sensing unit is positioned to detect scintillations along an axis substantially parallel to the common axis.

4. The radiation imaging apparatus of claim 3 wherein the first and second means comprise crystals each having a substantially rectangular cross-section in a plane substantially parallel to the common axis and having substantially planar surfaces opposite the common axis.

5. The radiation imaging apparatus of claim 4 wherein the joining means has a substantially triangular cross-section in a plane substantially perpendicular to the common axis and has a substantially planar surface parallel to and opposite the common axis.

6. The radiation imaging apparatus of claim 4 wherein the joining means comprises a plurality of UV transmitting plexiglas bridges.

7. The radiation imaging apparatus of claim 5 wherein a unit of the converting means is on one of the planar surfaces of the joining means.

8. The radiation imaging apparatus of claim 5 wherein the joining means comprises a plurality of glass bridges.

9. The radiation imaging apparatus of claim 8 wherein the glass bridges are prisms.

10. The radiation imaging apparatus of claim 1 comprising a single array of sensing units, each sensing unit providing a signal having a value which is representative of the position of the sensing unit in the array.

11. The radiation imaging apparatus of claim 10 further comprising means for determining the position of a scintillation.

12. The radiation imaging apparatus of claim 11 wherein the signal includes x, y, and z components and wherein the means for determining comprises means for summing x components, means for summing y components, and means for summing z components of all the sensing units.

13. The radiation imaging apparatus of claim 12 wherein each signal further includes a parameter which is a function of the energy ionizing radiation bombarding the scintillation producing means and wherein the means for determining comprises means for summing the signals of all of the sensing units for providing an energy signal.

14. The radiation imaging apparatus of claim 10 wherein said scintillation producing means comprises four planar bodies forming an open ended box-like structure substantially coaxial with the common axis, wherein the joining means comprises four triangular bodies, one located between two adjacent planar bodies and wherein the array includes at least eight PMTs, one each associated with an exterior planar surface of each planar body and each triangular body.

15. The radiation imaging apparatus of claim 1 further comprising light transmissive means having substantially planar exterior faces between the first and second means and the converting means.

16. The radiation imaging apparatus of claim 1 wherein the first and second means comprise planar bodies forming an oblique angle having vertex along an axis parallel to a common axis along which a specimen for emitting ionizing radiation is located.

17. The radiation imaging apparatus of claim 16 wherein the joining means has a substantially trapezoidal cross-section substantially perpendicular to the common axis and has substantially planar exterior faces.

18. The radiation imaging apparatus of claim 1 wherein the first and second means are composed of a crystalline material of sodium iodide.

19. The radiation imaging apparatus of claim 1 wherein the sensing units have respective coordinate positions relative to the common axis, and the apparatus further comprises means for computing a position value for a scintillation which is a function of a set of weighting factors representative of the coordinate position of the sensing unit relative to the common axis.

20. The radiation imaging apparatus of claim 19 for use with a specimen emitting ionizing radiation and further comprising means for producing a representation of the specimen from the values computed by the computing means.

21. The radiation imaging apparatus of claim 20 further comprising means for generating a tomographic display utilizing position value information produced by the computing means.

22. A radiation imaging apparatus for use with a specimen emitting ionizing radiation comprising:
  a scintillation assembly having a common axis along which the specimen is positioned and including a plurality of bodies having a substantially rectangular surface parallel to the common axis for producing scintillations in response to bombardment by the ionizing radiation from the specimen, each surface bordered in part by an edge;
  joining means located between adjacent edges of the bodies for joining the bodies in an open ended box-like structure substantially coaxial with the common axis, the joining means for transmitting light emitted from the edges of the bodies as a result of the scintillations produced by the bodies;
  means for converting light transmitted from the surface of the scintillation means and light transmitted by the joining means to electrical outputs including a plurality of scintillation sensing units located on the outside of the bodies and on the joining means.

23. The radiation imaging apparatus of claim 22 further comprising means for collimating the ionizing radiation bombarding the bodies perpendicular to the common axis.

24. The radiation imaging apparatus of claim 22 wherein the joining means has substantially triangular cross-sections substantially perpendicular to the common axis and having substantially planar exterior faces.

25. The radiation imaging apparatus of claim 24 wherein the joining means comprises a plurality of UV transmitting plexiglas bridges.

26. The radiation imaging apparatus of claim 24 wherein a unit of the converting means is located adjacent one of the planar exterior faces of the joining means.

27. The radiation imaging apparatus of claim 24 wherein the joining means comprises a plurality of glass bridges.

28. The radiation imaging apparatus of claim 27 wherein the glass bridges are prisms.

29. The radiation imaging apparatus of claim 22 comprising a single array of sensing units, each sensing unit providing a signal having a value which is representative of the position sensing unit in the array.

30. The radiation imaging apparatus of claim 29 further comprising means for determining the position of a scintillation.

31. The radiation imaging apparatus of claim 30 wherein said scintillation producing means comprises four planar bodies forming the open ended box-like structure, wherein the joining means comprises four triangular bodies, one located between two adjacent planar bodies and wherein the array includes at least eight PMTs, one each associated with an exterior planar surface of each planar body and each triangular body.

32. A radiation imaging method for use with a first and a second scintillation body comprising the steps of:
  producing scintillations in response to bombardment by ionizing radiation, each said scintillation body having a surface bordered in part by an edge, the edge of the first body adjacent the edge of the second body;
  transmitting light emitted from the edges of the first and second bodies as a result of scintillations produced by the first and second bodies by a third body located between the edges of the first and second bodies; and
  converting the scintillations to electrical outputs including a plurality of scintillation sensing units on the first and second scintillation bodies and on the third body.

33. The radiation imaging method of claim 32 further comprising the step of collimating the ionizing radiation bombarding the first and second scintillation bodies substantially perpendicular to a common axis.

* * * * *